United States Patent [19]

Winter et al.

[11] Patent Number: 4,665,185

[45] Date of Patent: May 12, 1987

[54] PROCESS FOR PREPARING NITROXYLS OF STERICALLY HINDERED AMINES

[75] Inventors: Roland A. E. Winter, Armonk; Roger F. Malherbe, Yonkers, both of N.Y.

[73] Assignee: Ciba-Geigy Corporation, Ardsley, N.Y.

[21] Appl. No.: 800,010

[22] Filed: Nov. 20, 1985

Related U.S. Application Data

[63] Continuation of Ser. No. 592,317, Mar. 22, 1984, abandoned.

[51] Int. Cl.$^4$ ............................................. C07D 211/94
[52] U.S. Cl. .................................. 546/184; 546/16; 546/192; 548/408; 548/542
[58] Field of Search .................... 546/184, 16, 192; 548/408, 542

[56] References Cited

U.S. PATENT DOCUMENTS 3,634,346 1/1972 McKeon et al. .................. 546/243 X

OTHER PUBLICATIONS

Chemical Abstracts, 95:96608f (1981), [Wang, C., et al., Hua Hsueh Tung Pao 1981, (4), 211–12].
V. Cholvald et al., Collection of Czech. Chem. Comm. 46, 1071 (1981).
Chem. Abst. 65, 8735 (1966).
Handbook Chemistry and Physics, 50th Ed., D-115 (1969).
A. R. Forrester et al., Organic Chemical of Stable Free Radicals, Academic Press, London (1968), p. 208.

Primary Examiner—Richard A. Schwartz
Attorney, Agent, or Firm—Luther A. R. Hall

[57] ABSTRACT

Nitroxyls of the formula

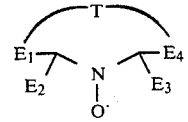

where $E_1$, $E_2$, $E_3$ and $E_4$ are independently an organic radical so that the carbon atoms to which they are attached are each a quaternary carbon and T is a divalent radical are prepared by the oxidation of the corresponding amine in an inert organic solvent with a hydroperoxide in the presence of a metal carbonyl, metal oxide or metal alkoxide catalyst in high yield and purity. The nitroxyls may be directly reduced to the corresponding hydroxylamines by catalytic hydrogenation. The nitroxyls are useful as polymerization inhibitors and the hydroxylamines as polymer stabilizers.

8 Claims, No Drawings

PROCESS FOR PREPARING NITROXYLS OF STERICALLY HINDERED AMINES

This is a continuation of application Ser. No. 592,317, filed on Mar. 22, 1984, now abandoned.

BACKGROUND OF THE INVENTION

The unique properties of nitroxyls, which have one unpaired electron, have found many applications. Nitroxyls have been used:
in the spin labeling of biologically active molecules (O. H. Griffiths, et al, Accounts Chem. Res. 2, 17 (1969));
as radical-polymerization inhibitors of chloroprene (M. B. Nieman, et al, Vysokomol. Soedin 8, 1237 (1966)=CA, 65, 17173a (1966));
of styrene (J. C. Bevington, et al, J. Chem. Soc 1956, 3506); and
of 2-vinylpyridine (I. V. Savinova, et al, Dokl. Akad. Nauk. SSSR 181, 1177 (1968)=CA, 70, 4643e (1969));
as inhibitors of the thermal and light-induced degradation of polyolefins (U.S. Pat. No. 3,431,233); and
of poly(vinyl chloride) (U.S. Pat. No. 3,547,874).

Hydroxylamines have found utility as stabilizers for polyolefins (U.S. Pat. No. 3,644,278), for polyesters (U.S. Pat. No. 3,408,422), for polyurethanes (spandex) (U.S. Pat. No. 3,926,909) and for conjugated diene polymers (U.S. Pat. No. 3,432,578).

A large number of nitroxyls have been prepared by oxidation of secondary amines with ozone (S. D. Razumovskii et al., Dokl. Akad. Nauk. SSSR 183, 1106 (1969)=CA, 70, 95987j (1969)); with dibenzoyl peroxide (A. M. Feldman et al, French Patent No. 1,360,030); with various peracids (G. Chapelet-Letourneux et al, Bull. Soc. Chim. 1965, 3283); or with tert-butylhydroperoxide (O. W. Maender, et al, J. Org. Chem. 34, 4072 (1969)).

Some limitations of the methods cited were mentioned by the last authors; namely that "Oxidizing systems involving hydrogen peroxide, tert-butylhydroperoxide or m-chloroperbenzoic acid were either too slow or ineffective".

The most useful method reported in the literature for the oxidation of secondary amines to nitroxyls requires the use of aqueous hydrogen peroxide in the presence of pertungstate ion (O. L. Lebedev, et al. Doklady Akad. Nauk. SSSR 140, 1327 (1961); and O. L. Lebedev, et al, CA, 56, 15479f (1962)).

Unfortunately, when the secondary amine is not very soluble in water, the reaction becomes so slow that it is not practical. The use of organic solvents miscible with water can alleviate this problem only if the system remains homogeneous, i.e., the amine does not precipitate or form a distinct phase. (E. J. Rauckman, et al, Synthetic Communications 5, 409 (1975)).

It would be desirable to manufacture nitroxyls by direct oxidation of the amine without the disadvantages of the prior art methods.

A liquid phase method of oxidation of cyclic amines was reported to produce lactams. U.S. Pat. No. 3,634,346 describes the oxidation of a cyclic amine having at least one unsubstituted methylene position adjacent to the ring nitrogen with a hydroperoxide in the presence of a metal ion-catalyst.

OBJECTS OF THE INVENTION

The object of this invention is to provide a process for the production of nitroxyl compounds by the oxidation of sterically hindered secondary amines.

A further object of this invention is to provide a facile process to the preparation of the corresponding hydroxylamine compounds by reduction of said nitroxyl compounds.

DETAILED DESCRIPTION

The instant invention pertains to a process for the efficient preparation of nitroxyls of sterically hindered amines by the oxidation of said amine using a hydroperoxide, in the presence of a small amount of a metal ion catalyst, at moderate temperature, for a short period of time to give the nitroxyl in high yield and purity.

Generically the instant invention is a process for the preparation of a nitroxyl of the formula

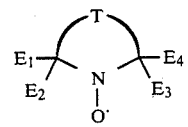

where the nitrogen atom is flanked by two quaternary carbon atoms, that is where $E_1$, $E_2$, $E_3$ and $E_4$ are independently an organic radical, and T is a divalent group required to form a cyclic 5- or 6-membered ring which comprises oxidizing an amine of the formula

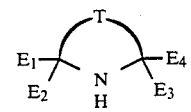

where $E_1$, $E_2$, $E_3$, $E_4$ and T have the meanings given above, dissolved in an inert organic solvent with a hydroperoxide in the presence of from 0.001 to 0.1 mole percent, based on the hydroperoxide, of a catalyst selected from the group consisting of the metal carbonyls, the metal oxides, the metal acetylacetonates and the metal alkoxides where the metal is selected from groups IVb, Vb, VIb, VIIb and VIII of the periodic table, at a temperature of 0° to 200° C., preferably 50° to 150° C., with the mole ratio of hydroperoxide to amine being 50:1 to 1:10, preferably 10:1 to 1:1.

More specifically, the instant invention is a process for the preparation of a nitroxyl of the formula

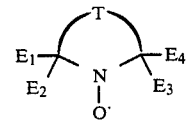

wherein
$E_1$ and $E_3$ are independently alkyl of 1 to 5 carbon atoms or phenyl,
$E_2$ and $E_4$ are independently alkyl of 1 to 5 carbon atoms, or
$E_1$ and $E_2$ together or $E_3$ and $E_4$ together or both $E_1$ and $E_2$ together and $E_3$ and $E_4$ together are tetramethylene or pentamethylene, and T is a divalent group required to form a cyclic 5- or 6-membered ring.

Preferably $E_1$, $E_2$, $E_3$ and $E_4$ are each methyl.

The nature of T is not critical to the instant process with the understanding that T remains inert, that is T remains chemically unchanged, to hydroperoxide attack or to subsequent catalytic reduction.

The amines which can be oxidized according to the invention contain a nitrogen atom which is substituted by two tertiary alkyl groups. Preferred compounds are cyclic amines having the two methylene adjacent to the ring nitrogen fully substituted by alkyl groups.

By way of illustration, 4-hydroxy-2,2,6,6-tetramethylpiperidine-1-oxyl, 4-benzoyloxy-2,2,6,6-tetramethylpiperidine-1-oxyl, 3-carbamoyl-2,2,5,5-tetramethylpyrrolidine-1-oxyl, N-(1-oxyl-2,2,6,6-tetramethylpiperidin-4-yl-)-ε-caprolactam, 3-oxyl-2,2,4,4-tetramethyl-7-oxa-3,20-diazaspiro[5.1.11.2]heneicosan-21-one, 4-aza-3,3-dimethyl-4-oxyl-1-oxaspiro[4.5]decane or 2,4,4-trimethyl-2-phenyl-3-oxyloxazolidine can be prepared from the corresponding secondary cyclic amine.

In the case of a reductive work-up, hydroxylamines are obtained. Illustrative examples of compounds prepared by this procedure are:

di-(1-hydroxy-2,2,6,6-tetramethylpiperidine-4-yl)sebacate

N-(1-hydroxy-2,2,6,6-tetramethylpiperidin-4-yl)-ε-caprolactam

The alkyl hydroperoxides which may be used in the process of this invention are tertiary-alkyl hydroperoxide, i.e., an alkane having a hydroperoxy group substituted on a tertiary carbon atom, or aralkyl hydroperoxides, wherein the hydroperoxy group is attached to the α-carbon of an aralkyl compound.

Suitable hydroperoxides are tert-butyl hydroperoxide, tert-amyl hydroperoxide, tert-hexyl hydroperoxide, tert-octyl hydroperoxide, ethylbenzene hydroperoxide, tetralin hydroperoxide or cumene (=isopropylbenzene) hydroperoxide.

Preferred hydroperoxides are tert-butyl hydroperoxide, tert-amyl hydroperoxide, ethylbenzene hydroperoxide, and cumene hydroperoxide. Expecially preferred are tert-butyl hydroperoxide and cumene hydroperoxide.

The reaction is conducted in the liquid phase in solvents which are substantially inert to the reactants and the products produced therefrom.

Illustrative suitable solvents are esters, such as butyl acetate; ketones, such as acetone; ethers such as dibutyl ether, dioxane or tetrahydrofuran; chlorinated solvents, such as methylene chloride, 1,2-dichloroethane; alkanes, such as hexane, decane; aromatic solvents, such as benzene, toluene, xylene, dichlorobenzene, isopropylbenzene (cumene).

In most instances the solvent is used in amounts up to 20 moles of solvent per mole of hydroperoxide.

In the preferred procedure the amine, the catalyst and the solvent are charged into a reaction vessel and the reaction mixture is maintained with agitation at the reaction temperature during the addition of peroxide. In another modification, reaction is effected continuously by contacting the amine and the hydroperoxide in a solvent containing the catalyst.

Suitable reaction temperatures vary from 0° to 200° C., but preferably from 50° to 150° C.

The catalysts are selected from the group consisting of the metal carbonyls, the metal oxides, the metal acetylacetonates and the metal alkoxides where the metal is selected from the groups IVb, Vb, VIb, VIIb and VIII of the periodic table. Examples of effective catalysts include vanadyl acetylacetonate, cobalt carbonyl, titanium (IV) isopropoxide, molybdenum hexacarbonyl, molybdenum trioxide and the like.

Especially preferred are molybdenum and titanium catalysts.

The reaction atmosphere can be ambient, oxygen enriched, or inert containing gases such as nitrogen, argon, and helium.

The amount of metal ion catalyst which is added to the reaction mixture is not narrowly critical and need only be added in amounts effective to initiate the reaction. An additional advantage of the instant process is that large amounts of catalyst are not required. The preferred range of catalyst is from 0.001 mole percent or lower to about 0.1 mole percent or higher based upon the hydroperoxide employed. Any amount can be used as long as it is catalytically effective. There is no limit to the upper range other than economic considerations.

At the end of the reaction, the product mixture is separated and the desired nitroxyl products are recovered by conventional methods.

Alternatively, the reaction mixture containing the desired nitroxyl compound may be used directly for the preparation of the corresponding hydroxylamine. The procedure required for this reduction of the nitroxyl to hydroxylamine may be a catalytic hydrogenation in the presence of a noble metal or nickel catalyst or a chemical reduction using zinc, borane or other classical reducing agents.

Thus, another aspect of the instant invention is a process for the preparaton of a hydroxylamine of the formula

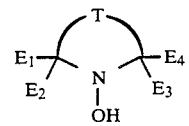

by the reduction of a nitroxyl of the formula

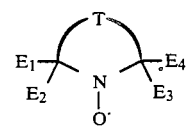

prepared by the instant process wherein $E_1$, $E_2$, $E_3$, $E_4$ and T are as defined above.

The following examples are presented for the purpose of illustration only and are not to be construed to limit the nature or scope of the instant invention in any manner whatsoever.

EXAMPLE 1

Preparation of 4-hydroxy-2,2,6,6-tetramethylpiperidin-1-oxyl

A reactor is charged with 50 ml of reagent-grade 1,2-dichloroethane, 8.5 g (0.054 mole) of 2,2,6,6-tetramethylpiperidin-4-ol and 0.10 g of molybdenum hexacarbonyl, Mo(CO)$_6$. The mixture is brought to reflux to give a clear solution. A dropping funnel is charged with 27 ml of 4M tert-butyl hydroperoxide in 1,2-dichloroethane and this solution is then added dropwise into the reactor, at a rate sufficient to maintain a gentle reflux without external heat.

The addition requires about 0.5 hour after which heat is applied for 4 hours. At this point gas chromatography (GC) showed <2% of unreacted amine. The reaction mixture is cooled, washed with 5% aqueous sodium sulfite. The aqueous phase is extracted with 50 ml of chloroform and the combined organic phases are dried over anhydrous magnesium sulfate. After evaporation of the solvents, the residue is crystallized from hexane, yielding 8.0 g (86% yield) of orange crystals, m.p. 69°–71° (lit. 71° C.)

(H. Lemaire, et al, Bull. Soc. Chim. France 1968, 886.).

EXAMPLE 2

When an equivalent amount of molybdenum (VI) oxide, $MoO_3$, is substituted for the molybdenum hexacarbonyl catalyst using the method of Example 1, after two hours reaction time more than 98% of the 2,2,6,6-tetramethylpiperidin-4-ol is converted to the corresponding N-oxyl compound as seen by gas chromatography.

EXAMPLE 3

When an equivalent amount of vanadyl acetylacetonate is substituted for the molybdenum hexacarbonyl catalyst using the method of Example 1, some insoluble material is obtained. The reaction is slower and after 2 hours only 31% of the amine is converted to the N-oxyl group as seen by gas chromatography.

EXAMPLE 4

Preparation of N-(1-oxyl-2,2,6,6-tetramethylpiperidin-4-yl)-ε-caprolactam

A sample of 25.2 g (0.1 mole) of N-(2,2,6,6-tetramethylpiperidine-4-yl)-ε-caprolactam is refluxed for 2 hours with 50 ml of 4M tert-butylhydroperoxide in the presence of 0.2 g of molybdenum hexacarbonyl, Mo(CO)$_6$ as described in Example 1, to provide 26.6 g of red solid (99% crude yield). Crystallization from hexane gives orange crystals, m.p. 152°–159° C.

Analysis: Calcd. for $C_{15}H_{27}N_2O_2$: C, 67.3; H, 10.1; N, 10.4. Found: C, 66.9; H, 9.9; N, 10.2.

EXAMPLE 5

When the molybdenum hexacarbonyl catalyst used in Example 4 is replaced by an equivalent amount of titanium tetraisopropoxide with a molar ratio of Ti(IV) to amine of 0.04, gas chromatography shows a 95% conversion of amine to the product of Example 4 after 5 hours.

EXAMPLE 6

Preparation of 4-benzoyloxy-2,2,6,6-tetramethylpiperidin-1-oxyl

When 13.1 g (0.05 mole) of (2,2,6,6-tetramethylpiperidin-4-yl)benzoate is oxidized as described by the method of Example 1, 9.5 g (69% yield) of orange crystals are isolated: m.p. 104°–106° C. (from methanol) (lit. m.p. 105° C.)

(V. A. Golubev, et al, Izv. Akad. Nauk. SSSR, Ser. Khim. 1965, 1927=CA, 64, 11164e (1966)).

EXAMPLE 7

Preparation of di-(1-hydroxy-2,2,6,6-tetramethylpiperidine-4-yl)sebacate

A solution containing 15.0 g (31.2 mmole) of di-(2,2,6,6-tetramethylpiperidin-4-yl)sebacate and 0.2 g molybdenum hexacarbonyl, Mo(CO)$_6$, (0.76 mmole) in 100 ml 1,2-dichloroethane is brought to reflux. Tert-butyl hydroperoxide (31.5 ml, 4M solution in 1,2-dichloroethane, 126 mmole) is added within 15 minutes and the solution is refluxed for 2.5 hours. The solution is cooled to room temperature, washed twice with 100 ml water, and the organic phase transferred to a hydrogenation flask. Catalytic hydrogenation is carried out at room temperature and with a hydrogen pressure of 40 psi (2.8 Kg/cm$^2$) to yield the hydroxylamine. The palladium/charcoal catalyst is removed by filtration and the solvent is evaporated. The solid is then recrystallized from ethanol-water (4:1, 250 ml), under a blanket of nitrogen to prevent oxidation of the product. A colorless solid is obtained (13.6 g, 85% yield) m.p. 129°–134° C. (lit. m.p. 101° C).

(E. F. Litvin, et al, Zh. Org. Khim. 6, 2365 (1970)=CA, 74, 64180u (1971))

EXAMPLE 8

Preparation of 3-oxyl-2,2,4,4-tetramethyl-7-oxa-3,20-diazaspiro[5.1.11.2]heneicosan-21-one A sample of 18.3 g (0.050 mole) of 2,2,4,4-tetramethyl-7-oxa-3,20-diazaspiro[5.1.11.2]heneicosan-21-one in 100 ml 1,2-dichloroethane is oxidized with 25 ml 4.0M tert-butylhydroperoxide in the same solvent, using 0.3 g molybdenum hexacarbonyl, Mo(CO)$_6$, catalyst. After refluxing for 3 hours, thin layer chromatography TLC shows >95% conversion.

EXAMPLE 9

Preparation of 1,1'-ethylenebis-(4-hydroxy-3,3,5,5-tetramethylpiperazin-2-one)

Oxidation of 16.9 (0.05 mole) of 1,1'-ethylenebis-(3,3,5,5-tetramethylpiperazin-2-one) gives a product, which is hydroxygenated without isolation as in Example 7. The hydrogenation catalyst is removed by filtration and the solvent evaporated, giving 15.1 g of light pink product (82% yield) m.p. 193° C. Recrystallization from ethyl acetate-methanol gives the title compound as a pure white solid, m.p. 200° C.

Analysis: Calcd for $C_{18}H_{34}N_4O_4$: C, 58.4; H, 9.3; N, 15.1. Found: C, 58.5; H, 9.3; N, 15.0.

NMR (DMSO-d6): 1.21 (s, 12H, 4 CH$_3$ axial); 1.43 (s, 12H, 4CH$_3$ equatorial); 3.20 and 3.50 (s, 8H, CH$_2$N); 4.60 (broad s, 2H, OH)

EXAMPLE 10

Preparation of 4-benzoyloxy-1-hydroxy-2,2,6,6-tetramethylpiperidine

A solution containing 26.2 g (0.1 mole) of (2,2,6,6-tetramethylpiperidin-4-yl)benzoate and 0.2 g molybdenum hexacarbonyl, Mo(CO)$_6$, in 20 ml toluene is warmed to 60° C. Cumene hydroperoxide (38.1 g of 80% solution, c.a. 0.2 mole) is added over a 45 minute period, giving a slightly exothermic reaction. Then the red solution is heated for another 30 minutes at 65° and transferred to a hydrogenation bottle.

The material is hydrogenated in the presence of 0.6 g 5% palladium-on-charcoal at 50 psi (3.5 Kg/cm$^2$) for 3 hours. The catalyst is then removed by filtration and washed with 100 ml of chloroform.

The filtrate is stripped of chloroform, and 100 ml of hot hexane is added. The mixture is cooled and 20.0 g (72% yield) of white precipitate is collected: m.p. 145°–149° C.

(lit 135°–146° C.; see reference in Example 6)

EXAMPLE 11

Preparation of 4-aza-3,3-dimethyl-4-oxyl-1-oxaspiro[4.5]decane

A solution of 32.1 g (0.19 mole) of 4-aza-3,3-dimethyl-1-oxaspiro[4.5]decane and 0.7 g of molybdenum hexacarbonyl, Mo(CO)$_6$, in 75 ml of toluene is heated to 90° C. and 20 ml of 4.4M tert-butylhydroperoxide in toluene is added over a 30-minute period. The solution is heated for another 45 minutes at 90° C. to give the corresponding 4-oxyl compound in situ. The starting substituted oxazolidine is prepared by the method given in J. Am. Chem Soc, 66, 1738 (1944). The 4-oxyl compound is described in J. Am. Chem Soc, 89, 3054 (1967).

EXAMPLE 12

Preparation of 2,4,4-trimethyl-2-phenyl-3-oxyloxazolidine

When using the procedure of Example 11, an equivalent amount of 2,4,4-trimethyl-2-phenyloxazolidine is substituted for the 4-aza-3,3-dimethyl-1-oxaspiro[4.5]-decane, the above-named compound is prepared.

What is claimed is:

1. A process for the preparation of a nitroxyl of the formula

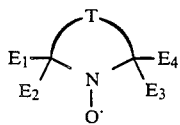

wherein
the nitrogen atom is flanked by two quaternary carbon atoms where $E_1$ and $E_3$ are independently alkyl of 1 to 5 carbon atoms of phenyl, $E_2$ and $E_4$ are independently alkyl of 1 to 5 carbon atoms, or $E_1$ and $E_2$ together or $E_3$ and $E_4$ together or both $E_1$ and $E_2$ together and $E_3$ and $E_4$ together are tetramethylene or pentamethylene, and T is a divalent group required to form a cyclic 5- or 6-membered ring, which comprises oxidizing an amine of the formula

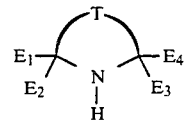

where $E_1$, $E_2$, $E_3$, $E_4$ and T have the meanings given above, dissolved in an inert organic solvent with a hydroperoxide in the presence of from 0.001 to 0.1 mole percent, based on the hydroperoxide, of a catalyst selected from the group consisting of the metal carbonyls, the metal oxides, the metal acetylacetonates and the metal alkoxides where the metal is selected from groups IVb, Vb, VIb, VIIb and VIII of the periodic table, at a temperature of 0° to 200° C., with the mole ratio of hydroperoxide to amine being 50:1 to 1:10.

2. A process according to claim 1 wherein $E_1$, $E_2$, $E_3$ and $E_4$ are each methyl.

3. A process according to claim 1 wherein the temperature is 50° to 150° C.

4. A process according to claim 1 wherein the mole ratio of hydroperoxide to amine is 10:1 to 1:1.

5. A process according to claim 1 wherein the hydroperoxide is tert-butyl hydroperoxide, tert-amyl hydroperoxide, ethylbenzene hydroperoxide or cumene hydroperoxide.

6. A process according to claim 4 wherein the hydroperoxide is tert-butyl hydroperoxide or cumene hydroperoxide.

7. A process according to claim 1 wherein the catalyst is vanadyl acetylacetonate, cobalt carbonyl, titanium (IV) isopropoxide, molybdenum hexacarbonyl or molybdenum trioxide.

8. A process according to claim 6 wherein the catalyst is titanium (IV) isopropoxide, molybdenum hexacarbonyl or molybdenum trioxide.

* * * * *